United States Patent
Burrell et al.

(10) Patent No.: US 7,518,721 B2
(45) Date of Patent: Apr. 14, 2009

(54) RAMAN-ACTIVE LATERAL FLOW DEVICE AND METHODS OF DETECTION

(75) Inventors: Michael Craig Burrell, Clifton Park, NY (US); Frank J. Mondello, Niskayuna, NY (US); Yuan-Hsiang Lee, Winchester, MA (US); Patrick Ronald Engel, Watertown, MA (US); Andrew David Pris, Niskayuna, NY (US)

(73) Assignee: GE Homeland Protection, Inc., Newark, CA (US)

( * ) Notice: Subject to any disclaimer, the term of this patent is extended or adjusted under 35 U.S.C. 154(b) by 56 days.

(21) Appl. No.: 11/223,353

(22) Filed: Sep. 9, 2005

(65) Prior Publication Data
US 2007/0059203 A1    Mar. 15, 2007

(51) Int. Cl.
*G01J 3/44* (2006.01)
(52) U.S. Cl. .............. 356/301; 435/288.7; 436/171; 422/82.05
(58) Field of Classification Search ............ 356/301
See application file for complete search history.

(56) References Cited

U.S. PATENT DOCUMENTS

| | | | |
|---|---|---|---|
| 6,514,767 B1 | 2/2003 | Natan | |
| 6,579,721 B1 | 6/2003 | Natan | |
| 2002/0123050 A1* | 9/2002 | Poponin | 435/6 |
| 2003/0059820 A1* | 3/2003 | Vo-Dinh | 435/6 |
| 2003/0166297 A1* | 9/2003 | Natan | 436/166 |
| 2003/0170613 A1* | 9/2003 | Straus | 435/5 |
| 2003/0231304 A1* | 12/2003 | Chan et al. | 356/301 |
| 2004/0135997 A1* | 7/2004 | Chan et al. | 356/301 |
| 2004/0150818 A1* | 8/2004 | Armstrong et al. | 356/301 |
| 2004/0179195 A1* | 9/2004 | Su et al. | 356/301 |
| 2005/0089901 A1 | 4/2005 | Porter et al. | |
| 2005/0110990 A1* | 5/2005 | Koo et al. | 356/301 |
| 2005/0123563 A1* | 6/2005 | Doranz et al. | 424/204.1 |
| 2005/0130163 A1 | 6/2005 | Smith et al. | |
| 2005/0250141 A1* | 11/2005 | Lambert et al. | 435/6 |
| 2005/0287552 A1* | 12/2005 | Lin et al. | 435/6 |

(Continued)

FOREIGN PATENT DOCUMENTS

WO    WO2006073439 A2    7/2006

OTHER PUBLICATIONS

J. Ni, et al., "Immunoassay readout method using extrinsic raman labels adsorbed on immunogold colloids", Anal. Chem. 71, 4903-4908, 1999.

(Continued)

*Primary Examiner*—Kara E Geisel
*Assistant Examiner*—Jonathon D Cook
(74) *Attorney, Agent, or Firm*—Richard A. DeCristofaro

(57) ABSTRACT

A lateral flow device is disclosed. The lateral flow device includes a substrate having a flow path and a detection zone disposed along the flow path. The detection zone includes an immobilized target-binding moiety directed against a target of a Raman-active complex. Also disclosed is a method of conducting a lateral flow assay and detection system. The method includes i) defining a flow path having a detection zone; ii) flowing a sample down the flow path; and iii) immobilizing a Raman-active complex if present, at the detection zone. The sample includes a Raman-active complex or a Raman-active tag.

36 Claims, 8 Drawing Sheets

U.S. PATENT DOCUMENTS

| | | | |
|---|---|---|---|
| 2006/0033910 A1* | 2/2006 | Sun et al. | 356/301 |
| 2006/0038990 A1* | 2/2006 | Habib et al. | 356/301 |
| 2006/0045807 A1* | 3/2006 | Zhang et al. | 422/82.05 |
| 2006/0146323 A1* | 7/2006 | Bratkovski et al. | 356/301 |
| 2006/0240572 A1* | 10/2006 | Carron et al. | 436/524 |
| 2007/0058165 A1* | 3/2007 | Mondello | 356/301 |
| 2008/0032420 A1* | 2/2008 | Lambert et al. | 436/514 |

OTHER PUBLICATIONS

S. P. Mulvaney, et al., "Glass-coated, analyte tagged nanoparticles: A new tagging system based on detection with surface-enhanced raman scattering", Langmuir, 19, 4784-4790, 2003.

D. S. Grubisha, et al., "Femtomolar detection of prostate-specific antigen: An immunoassay based on surface-enhanced raman scattering and immunogold labels", Anal. Chem., 75(21) 5936-43, 2003.

* cited by examiner

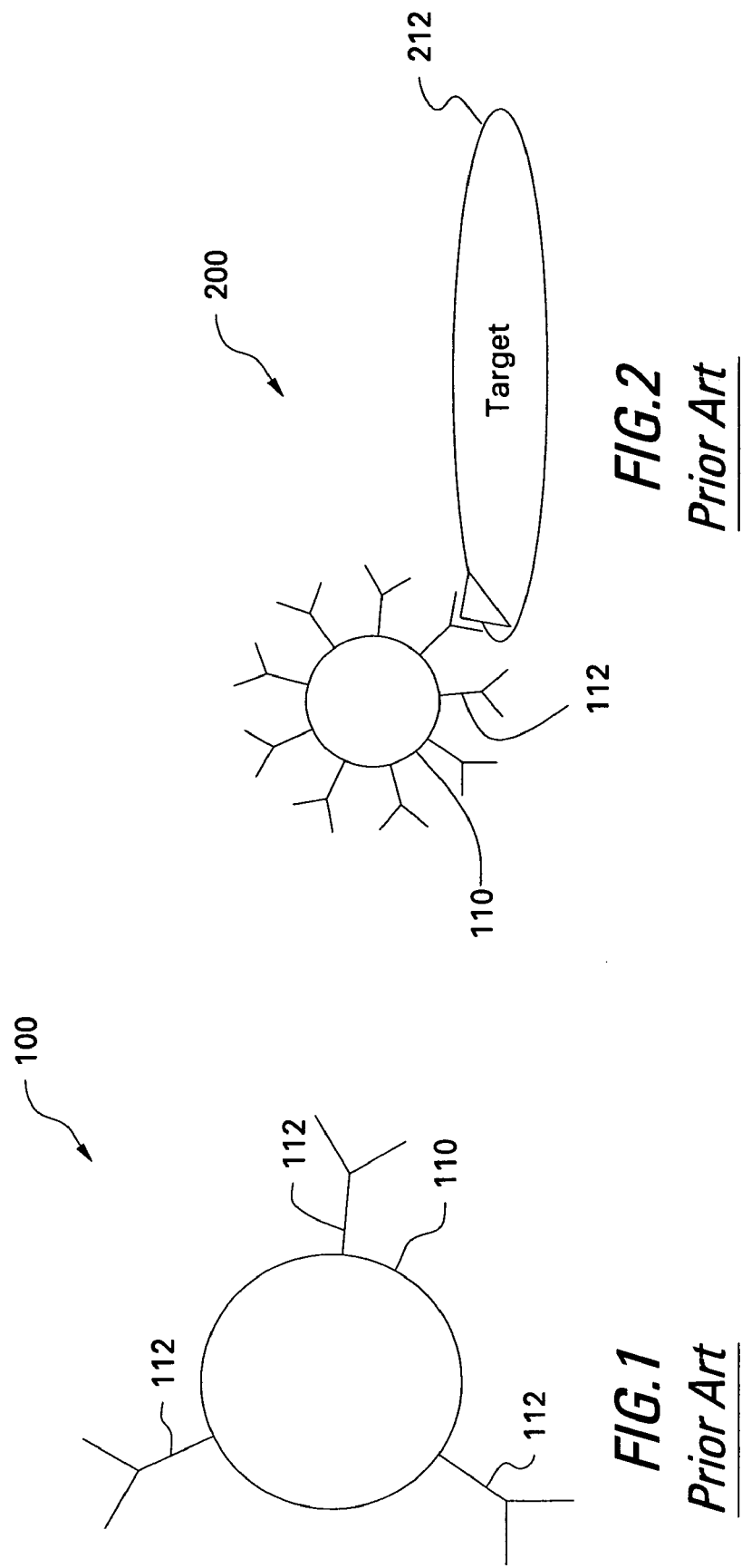

RAMAN-ACTIVE LATERAL FLOW DEVICE AND METHODS OF DETECTION

BACKGROUND

The invention includes embodiments that relate to Raman-active assays and surface enhanced Raman-active assays. Particularly, the invention includes embodiments that are directed to Raman-active assays and surface enhanced Raman-active lateral flow devices, assays, and methods.

DESCRIPTION OF RELATED ART

Some assays or methods for detecting the presence of pathogenic organisms or other materials are known. Also known are Raman and surface enhanced Raman-active tags 100. FIG. 1 is a schematic representation of a Raman-active tag 100 that includes one or more target-binding moieties 112 attached to a Raman-active particle 110. The target-binding moiety 112 on the Raman-active tag 100 can attach to one or more targets 212 to form a Raman-active complex 200 as shown in FIG. 2.

A need exists for methods and systems for detecting the presence of pathogenic organisms or other materials. It may be desirable to have a device, system, or method that detects organisms or materials. It may also be desirable to have a device, system or method that quantifies or identifies organisms or materials.

BRIEF DESCRIPTION

The purpose of embodiments of the invention will be set forth and apparent from the description that follows, as well as will be learned by practice of the embodiments of the invention. Additional advantages will be realized and attained by the methods and systems particularly pointed out in the written description and claims hereof, as well as from the appended drawings.

Lateral flow devices and methods for detecting the presence of target pathogenic organism or other material using Raman, surface-enhanced Raman, resonance Raman, or Raman-active tags are disclosed.

An embodiment provides a lateral flow device. The lateral flow device includes a substrate having a flow path and a detection zone disposed along the flow path. The detection zone includes an immobilized target-binding moiety directed against a target of a Raman-active complex.

Another embodiment provides a detection system. The detection system includes a lateral flow device and a Raman spectrometer. The lateral flow device includes a substrate having a flow path and a detection zone disposed along the flow path. The Raman spectrometer is capable of detecting a Raman-active complex at the detection zone.

Another embodiment provides a method of conducting a lateral flow assay. The method includes i) defining a flow path having a detection zone; ii) flowing a sample down the flow path; and iii) immobilizing a Raman-active complex, if present, at the detection zone. The sample includes a Raman-active complex or a Raman-active tag.

Another embodiment provides a method of detecting the presence of a target. The method includes i) conducting a lateral flow assay having a flow path, wherein the flow path has a plurality of detection zones; and ii) flowing a sample down the flow path. The sample includes a Raman-active complex or a Raman-active tag and is suspected of having a plurality of targets.

The accompanying figures, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

FIG. 1 is a schematic representation of a known unattached Raman-active tag;

FIG. 2 is a schematic representation of a known Raman-active complex;

DETAILED DESCRIPTION

Figure 3A:
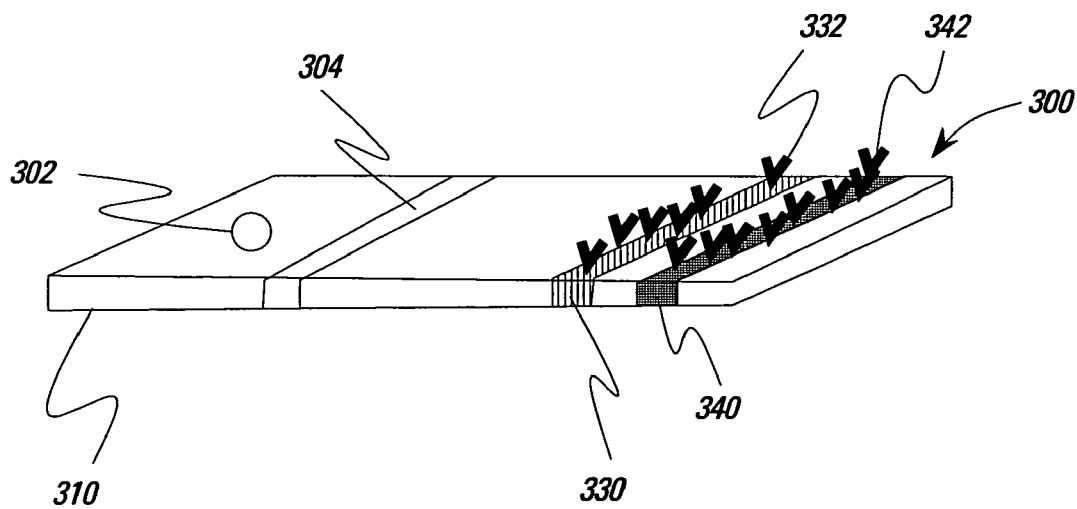
FIG. 3A-3C are schematic representations of a lateral flow device in accordance with an embodiment of the invention.

Reference will now be made in detail to exemplary embodiments of the invention, which are illustrated in the accompanying figures and examples. Referring to the drawings in general, it will be understood that the illustrations are for the purpose of describing a particular embodiment of the invention and are not intended to limit the invention thereto.

Whenever a particular embodiment of the invention is said to comprise or consist of at least one element of a group and combinations thereof, it is understood that the embodiment may comprise or consist of any of the elements of the group, either individually or in combination with any of the other elements of that group. Furthermore, when any variable occurs more than one time in any constituent or in formula, its definition on each occurrence is independent of its definition at every other occurrence. Also, combinations of substituents and/or variables are permissible only if such combinations result in stable compounds.

With reference to FIG. 3, there is shown one embodiment of a lateral flow device 300. The lateral flow device 300 includes a substrate 310 having one or more flow paths 320 and one or more detection zones 330. The detection zone 330 is disposed along the flow path 320. The detection zone 330 includes one or more immobilized target-binding moieties 332 directed against a target of a Raman-active complex. In a particular embodiment, the lateral flow device may have one or more control zones 340. The control zone 340 is disposed along the flow path 320 down flow from the detection zone 330 and includes one or more immobilized particle-binding-moieties 342 directed against a Raman-active tag. The lateral flow device 300 may also include one or more sample zones 302 for depositing a sample and one or more contact zones 304.

Raman Active Tag and Raman Active Complex

Unless noted otherwise, the word "Raman" and "Raman-active" includes Raman, surface-enhanced Raman, resonance Raman, and surface-enhanced resonance Raman spectroscopies.

In one embodiment, the Raman-active tag is immuno-functionalized. Immuno-functionalized Raman-active tags are capable of detecting the presence of one or more targets, such as pathogenic organisms or other materials. Immuno-functionalized Raman-active tags include Raman-active tags attached to one or more target-binding moieties such as antibodies. The target-binding moiety can be attached to the Raman-active tag and used to form a Raman-active complex. Attached means the target-binding moiety is covalently or non-covalently connected to a target.

Raman Active Particle of the Raman-Active Tag or Raman-Active Complex

The Raman-active particles may be of various size, shape and materials. In one embodiment, the Raman-active particle includes a core particle, a coating, and a Raman-active analyte. It should be appreciated that one or more core particles, coatings, and analytes may be included within the Raman-active particle. The analyte is at least partially within the coating and the coating at least partially covers the core particle. In a particular embodiment, the coating substantially covers the core particle.

In one embodiment, the core particle has a metallic surface. The core particle may include a metal such as, but not limited to, Au, Ag, Cu, Ni, Pd, Pt, Na, Al, and Cr, either individually or through any combination thereof. The core particle may include any other inorganic or organic material provided the surface of the core particle is metallic. In a particular embodiment, the core particle comprises Au.

The shape of the core particle may vary. For example, the core particle may be in the shape of a sphere, fiber, plate, cube, tripod, pyramid, rod, tetrapod, or any non-spherical object. In one embodiment, the core particle is substantially spherical.

The size of the core particle also may vary and can depend on its composition and intended use. In one embodiment, the core particles have an average diameter in a range from about 1 nm to about 500 nm. In another embodiment, the core particles have an average diameter less than about 100 nm. In yet another embodiment, the core particles have an average diameter in a range from about 12 nm to about 100 nm.

In one embodiment, the coating includes a material which stabilizes the Raman-active particle against aggregation. The coating stabilizes the Raman-active particle in one way by inhibiting aggregation of Raman-active particles. The coating is sufficiently thick to stabilize the Raman-active particle. In one embodiment, the coating has a thickness in a range from about 1 nm to about 500 nm. In another embodiment, the coating has a thickness in a range from about 5 nm to about 30 nm.

In one embodiment, the coating includes an elemental oxide. In a particular embodiment, the element in the elemental oxide includes silicon. The percentage of silicon may depend on one or more factors. Such factors may include the intended use of the Raman-active particle, the composition of the core particle, the degree to which the coating is to be functionalized, the desired density of the coating for a given application, the desired melting point for the coating, the identity of any other materials which constitute the coating, and the technique by which the Raman-active particle is to be prepared. In one embodiment, the element in the elemental oxide of the coating includes at least about 50-mole % silicon. In another embodiment, the element in the elemental oxide of the coating includes at least about 70-mole %. Yet, in another embodiment, the element in the elemental oxide of the coating comprises substantially silicon.

In yet another embodiment, the coating includes a composite. A composite coating may include oxides of one or more elements such as, but not limited to, Si, B, Al, Ga, In, Sc, Y, La, Ti, Zr, Hf, V, Nb, Ta, Cr, Mn, Fe, Co, Ni, Li, Na, K, Rb, Cs, Be, Mg, Ca, Sr, Ba, Zn, Cd, Ge, Sn, and Pb. Furthermore, the coating may include multilayer coatings. Each of the coating layers in the multilayer coating individually may include different coating compositions, such as 50-mole % silicon oxide in one coating layer and a composite coating in another coating layer.

The Raman-active particle includes one or more Raman-active analytes. In one embodiment, the Raman-active analyte is a molecule that exhibits Raman scattering when in the vicinity of a metallic core or a metallic surface of a core particle. Examples of Raman-active analytes include, but are not limited to, 4-mercaptopyridine, 2-mercaptopyridine (MP), trans-bis(pyridyl)ethylene (BPE), naphthalene thiol (NT), 4,4'-dipyridyl (DPY), quinoline thiol (QSH), and mercaptobenzoic acid, either individually or any combination thereof. In a particular embodiment, the Raman-active analyte includes trans-bis(pyridyl)ethylene and or quinoline thiol.

In one embodiment, the Raman-active analyte is at least partially within the coating. The Raman-active analyte can be at least partially within the coating in various orientations, such as, but not limited to, dispersed within the coating, within and around the coating, or embedded within the coating. Furthermore, a plurality of analytes may be within the coating. The plurality of analytes may be within the coating at a plurality of sites or at a single site. It should be appreciated that each of the analytes may be within the coating by a different mode, such as dispersed within the coating, around the coating, or embedded within the coating.

The Raman-active particle may include one core particle within a coating or multiple core particles within a coating. The multiple core particles are non-aggregated or closer together. There may be particular advantages associated with Raman-active particles that have one core particle within a coating or multiple core particles within a coating. The selection as to how many core particles should be contained within a coating may depend on the particular application for which the Raman-active particles are being used. Adjusting process conditions may be effective in obtaining Raman-active particles with a single core particle contained in the coating. For example, the coating may also stabilize a core particle against aggregating with another core particle.

The Raman-active particle may vary in shape and size. In one embodiment, the Raman-active particles are substantially spherical and have an average diameter in a range less than about 1000 nm. In a particular embodiment, the Raman-active particle has an average diameter less than about 100 nm.

In one embodiment, the Raman-active particle includes one or more linkers. The linker binds to the core particle and interacts with the coating. The linker allows or facilitates the coating to attach to the core particle. The linker may be a molecule having a functional group. The functional group can bind to the metal surface of the core particle and bind to the coating. An example of a linker is alkoxysilanes. Examples of alkoxysilanes include trialkoxysilanes. Trialkoxysilane linkers may be used to deposit coatings comprising silica. Suitable trialkoxysilane linkers include, but are not limited to, aminopropyl trimethoxysilane (APTMS), aminopropyl triethoxysilane, mercaptopropyl trimethoxysilane, mercaptopropyl triethoxysilane, hydroxypropyl trimethoxysilane, and hydroxypropyl triethoxysilane, either individually or in any combinations thereof.

When more than one analyte, coating, linker, and core particle are present, the definition on each occurrence is independent of the definition at every other occurrence. Also, combinations of an analyte, coating, linker, and core particle are permissible if such combinations result in stable Raman-active particles. Also, methods in combining an analyte, coating, linker, and core particle are permissible if such combinations result in stable Raman-active particles.

Targets and Target-Binding Moieties

Target-binding moieties are capable of attaching to the target, directly or indirectly. The lateral flow device is not limited by how the target-binding moieties attach to the target. Examples of attaching include, but are not restricted to, electrostatically, chemically, and physically. Examples of target-binding moieties include, but are not limited to, antibodies, aptamers, polypeptides, peptides, nucleic acids, avidin, streptavidin, and derivatives of avidin and streptavidin, either individually or in any combination thereof. The Raman-active tag may include one target-binding moiety or a plurality of target-binding moieties. The plurality of target-binding moieties may all be of the same kind of target-binding moieties or different kinds of target-binding moieties capable of attaching to different types of target.

Targets include living or not living targets. Examples of targets include, but are not limited to, prokaryotic cells, eukaryotic cells, viruses, proteins, polypeptides, toxins, liposomes, beads, ligands, amino acids, and nucleic acids, either individually or in any combinations thereof. The target also includes extracts of the above, living or not living targets.

Examples of prokaryotic cells include, but are not limited to, bacteria also include extracts thereof. Examples of eukaryotic cells include, but are not limited to, yeast cells, animal cells and tissues. Examples of toxins include, but are not limited to, anthrax. Examples of beads include, but are not limited to, latex, polystyrene, silica and plastic.

The term "peptide" refers to oligomers or polymers of any length wherein the constituent monomers are alpha amino acids linked through amide bonds, and encompasses amino acid dimers as well as polypeptides, peptide fragments, peptide analogs, naturally occurring proteins, mutated, variant or chemically modified proteins, fusion proteins, and the like. The amino acids of the peptide molecules may be any of the twenty conventional amino acids, stereoisomers (e.g., D-amino acids) of the conventional amino acids, structural variants of the conventional amino acids, e.g., iso-valine, or non-naturally occurring amino acids such as $\alpha,\alpha$-disubstituted amino acids, N-alkyl amino acids, $\beta$-alanine, naphthylalanine, 3-pyridylalanine, 4-hydroxyproline, O-phosphoserine, N-acetylserine, N-formylmethionine, 3-methylhistidine, 5-hydroxylysine, and nor-leucine. In addition, the term "peptide" encompasses peptides with post-translational modifications such as glycosylations, acetylations, phosphorylations, and the like.

The term "oligonucleotide" is used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. The term also includes modifications, such as by methylation and/or by capping, and unmodified forms of the oligonucleotide. More particularly, the term includes polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholine (commercially available from the Anti-Virals, Inc., Corvallis, Oreg., as Neugene) polymers, and other synthetic sequence-specific nucleic acid polymers, providing that the polymers contain nucleobases in a configuration that allows for base pairing and base stacking, such as is found in DNA and RNA. There is no intended distinction in length between the terms "polynucleotide", "oligonucleotide", "nucleic acid" and "nucleic acid molecule", and these terms refer only to the primary structure of the molecule. Thus, these terms include, for example, 3'-deoxy-2',5'-DNA, oligodeoxyribonucleotide N3'P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps", substitution of one or more of the naturally occurring nucleotides with an analog, internucleotide modifications such as, for, example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes other kinds of nucleic acids such as, but not limited to, locked nucleic acids (LNAs).

The terms "nucleoside" and "nucleotide" also include those moieties that contain not only the known purine and pyrimidine bases, but also other heterocyclic bases, which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base that form hydrogen bonds to a respective complementary pyrimidine or purine. The resultant modified nucleotidic unit optionally may form a base pair with other such modified nucleotidic units but not with A, T, C, G or U. Basic sites may be incorporated which do not prevent the function of the polynucleotide. Some or all of the residues in the polynucleotide can optionally be modified in one or more ways.

The term "antibody" as used herein includes antibodies obtained from both polyclonal and monoclonal preparations, as well as hybrid (chimeric) antibody molecules; F(ab')2 and F(ab) fragments; Fv molecules (noncovalent heterodimers); single-chain Fv molecules (sFv); dimeric and trimeric antibody fragment constructs; humanized antibody molecules; and any functional fragments obtained from such molecules, wherein such fragments retain specific-binding properties of the parent antibody molecule. In one embodiment, the target is attached to one Raman-active complex or a plurality of Raman-active complexes.

Substrate

The substrate may vary in size, shape, and material. In one embodiment, the substrate includes nitrocellulose membrane. Other membrane types include cellulose acetate, glass fiber, polyethersulfone, nylon, or other polymers, either individually or in combinations thereof. In one embodiment, the substrate may have dimensions from about 5 mm to about 580 mm in length, from about 1 mm to about 150 mm in width, and from about 0.0001 mm to about 5 mm thick. In another embodiment, the substrate has a dimension in a range of 58 mm length×5 mm width×0.5 mm thickness. The flow paths of a plurality of raman-active tags or complexes can be shared, or similar or be unique.

Flow Path

Figure 3B:
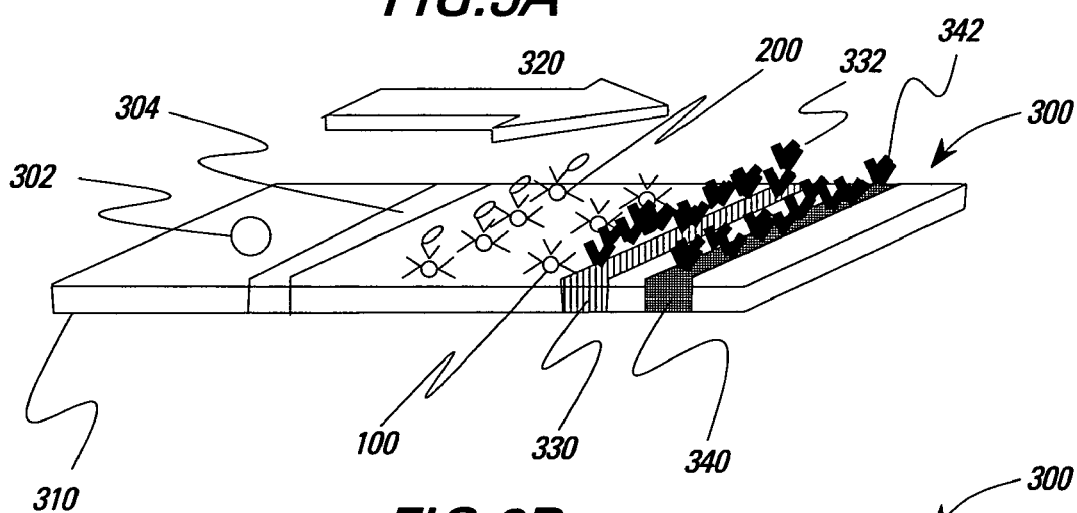
Figure 3C:
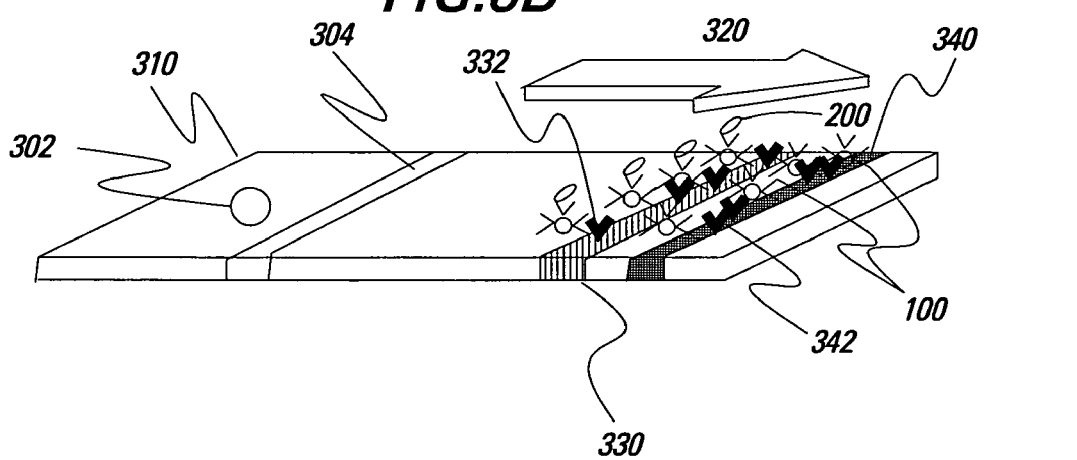

A flow path 320 is the direction of movement of a Raman active tag or Raman active complex, as shown by the movement of the arrow from FIG. 3A to FIG. 3B to FIG. 3C. The sample containing the suspected target and the Raman-active tags or Raman-active complex may be drawn by capillary action from the point of deposit (such as the sample zone 302 in FIG. 3A) across the substrate to another location, such as the detection zone or contact zone as shown in FIG. 3B and FIG. 3C, as shown by the movement of the flow path 320 arrow. In one embodiment, the sample is a liquid, and the movement is assisted by an absorbent pad contacting the substrate.

Sample and Contact Zone

In one embodiment, the sample is deposited on the sample zone 302. In one embodiment, the Raman-active particle and the target come in contact at the contact zone 304, such as when a sample containing the Raman-active particle and a sample containing the suspected target are deposited sequentially. The contact zone is located upflow from the detection zone. In another embodiment, a Raman-active particle and target are already in contact with each other before the contact zone, such as when the sample includes the Raman-active particle and the suspected target and is deposited simultaneously.

Detection Zone

The detection zone includes one or more immobilized target-binding moieties directed against a target of a Raman-active complex. In one embodiment, the immobilized target-binding moiety may attach to a Raman-active complex directly or via an intermediary or linker. Immobilized means at least partially immobilized such that the target-binding moiety at least partially attaches to the substrate. Approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value. In at least some instances, the approximating language may correspond to the precision of an instrument for measuring the value. Similarly, "immobilized" may be used in combination with a term, and may include an insubstantial number or trace amount of movement while still being considered immobilized.

The detection zone may include a plurality of immobilized target-binding moieties directed against a target of a Raman-active complex. The lateral flow device is not limited by how the target-binding moieties are immobilized at the detection zone. Examples of immobilizing include, but are not restricted to, electrostatically, chemically, and physically adsorbing, either individually or in combination, wherein each of the plurality of target-binding moieties may be immobilized by different modes.

Furthermore, the plurality of immobilized target-binding moieties may be of the same or similar kind capable of attaching to the same type of targets, such that the detection zone can be capable of capturing a plurality of the same or similar kinds of targets. The plurality of immobilized target-binding moieties may also be of differing kind capable of attaching to different types of target, such that the detection zone can capture a plurality of different kinds of targets. Detection of the plurality of the targets is then based on the presence of Raman signal after removing any Raman-active tags that are unattached to a target from the test mixture.

A plurality of detection zones may be present, in which at least some may be partially co-located or spatially separated. The detection zone and the control zone may also be partially co-located or spatially separated.

Examples of the immobilized target-binding moieties include antibodies, aptamers, nucleic acids, selective ligands, and polypeptides, either individually or in any combination thereof. Examples of selective ligands include porphyrins, ethylenediaminetetraacetic acid (EDTA), and zinc fingers. Selective ligand means a ligand selective for a particular target or targets.

Other non-limiting examples of immobilized target-binding moieties include, but are not limited to, proteins, peptides, polypeptides, glycoproteins, lipoproteins, phospholipids, oligonucleotides, or the like, e.g. enzymes, immune modulators, receptor proteins, antibodies and antibody fragments, which preferentially bind marker substances that are produced by or associated with the target site.

Proteins are known that preferentially bind marker substances that are produced by or associated with lesions. For example, antibodies can be used against cancer-associated substances, as well as against any pathological lesion that shows an increased or unique antigenic marker, such as against substances associated with cardiovascular lesions, for example, vascular clots including thrombi and emboli, myocardial infarctions and other organ infarcts, and atherosclerotic plaques; inflammatory lesions; and infectious and parasitic agents.

Cancer states include carcinomas, melanomas, sarcomas, neuroblastomas, leukemias, lymphomas, gliomas, myelomas, and neural tumors. Infectious diseases include those caused by body invading microbes or parasites.

The protein substances useful as immobilized target-binding moieties include protein, peptide, polypeptide, glycoprotein, lipoprotein, or the like; e.g. hormones, lymphokines, growth factors, albumin, cytokines, enzymes, immune modulators, receptor proteins, antibodies and antibody fragments. The protein substances of particular interest are antibodies and antibody fragments. The terms "antibodies" and "antibody fragments" mean generally immunoglobulins or fragments thereof that specifically bind to antigens to form immune complexes.

The antibody may be a whole immunoglobulin of any class; e.g., IgG, IgM, IgA, IgD, IgE, chimeric or hybrid antibodies with dual or multiple antigen or epitope specificities. It can be a polyclonal antibody, particularly a humanized or an affinity-purified antibody from a human. It can be an antibody from an appropriate animal; e.g., a primate, goat, rabbit, mouse, or the like. If a paratope region is obtained from a non-human species, the target may be humanized to reduce immunogenicity of the non-human antibodies, for use in human diagnostic or therapeutic applications. Such a humanized antibody or fragment thereof is also termed "chimeric." For example, a chimeric antibody comprises non-human (such as murine) variable regions and human constant regions. A chimeric antibody fragment can comprise a variable binding sequence or complementarity-determining regions ("CDR") derived from a non-human antibody within a human variable region framework domain. Monoclonal antibodies are also suitable because of their high specificities. Useful antibody fragments include $F(ab')_2$, $F(ab)_2$, Fab', Fab, Fv, and the like including hybrid fragments. Particular fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. An antibody fragment can include genetically engineered and/or recombinant proteins, whether single-chain or multiple-chain, which incorporate an antigen-binding site and otherwise function in vivo as immobilized target-binding moieties in substantially the same way as natural immunoglobulin fragments. The fragments may also be produced by genetic engineering.

Mixtures of antibodies and immunoglobulin classes can be used, as can hybrid antibodies. Multispecific, including bispecific and hybrid, antibodies and antibody fragments are sometimes desirable for detecting and treating lesions and comprise at least two different substantially monospecific antibodies or antibody fragments, wherein at least two of the antibodies or antibody fragments specifically bind to at least two different antigens produced or associated with the targeted lesion or at least two different epitopes or molecules of a marker substance produced or associated with the targeted lesion. Multispecific antibodies and antibody fragments with dual specificities can be prepared analogously to anti-tumor marker hybrids.

Suitable MAbs have been developed against most of the microorganisms (bacteria, viruses, protozoa, other parasites) responsible for the majority of infections in humans, and many have been used previously for in vitro diagnostic purposes. These antibodies, and newer MAbs that can be generated by conventional methods, are also appropriate for use.

Proteins useful for detecting and/or treating cardiovascular lesions include fibrin-specific proteins; for example, fibrinogen, soluble fibrin, antifibrin antibodies and fragments, fragment $E_1$ (a 60 kDa fragment of human fibrin made by controlled plasmin digestion of crosslinked fibrin), plasmin (an enzyme in the blood responsible for the dissolution of fresh thrombi), plasminogen activators (e.g., urokinase, streptokinase and tissue plasminogen activator), heparin, and fibronectin (an adhesive plasma glycoprotein of 450 kDa) and platelet-directed proteins; for example, platelets, antiplatelet antibodies, and antibody fragments, anti-activated platelet antibodies, and anti-activated platelet factors.

In one embodiment, the immobilized target-binding moiety includes a MAb or a fragment thereof that recognizes and binds to a heptapeptide of the amino terminus of the β-chain of fibrin monomer. Fibrin monomers are produced when thrombin cleaves two pairs of small peptides from fibrinogen. Fibrin monomers spontaneously aggregate into an insoluble gel, which is further stabilized to produce blood clots.

The disclosure of various antigens or biomarkers that can be used to raise specific antibodies against them (and from which antibodies fragments may be prepared) serves only as examples, and is not to be construed in any way as a limitation of the invention.

Control Zone

The control zone includes one or more immobilized particle-binding moieties directed against and capable of attaching to a Raman-active tag. Immobilized means at least partially attached to the substrate. The lateral flow device is not limited by how the particle-binding moieties are immobilized at the control zone. Examples of immobilizing include, but are not restricted to, electrostatically, chemically, and physically adsorbing, either individually or in combination, wherein each of the plurality of particle-binding moieties may be immobilized by different modes. In one embodiment, the detection zone and the control zone are at least partially co-located or spatially separated along the flow path. Examples of the immobilized particle-binding moieties include, but are not limited to, antibodies, aptamers, nucleic acids, and polypeptides, either individually or in any combination thereof.

Another aspect of the invention includes a detection system. The detection system includes a lateral flow device and a Raman spectrometer capable of detecting a Raman-active complex, if present, at the detection zone. Examples of Raman spectrometers include dispersive grating, interferometer, and tunable filters, employing single or multiple detectors, and with varying light sources, such as laser, light emitting diode, and white light. Examples of single channel detectors include photo multiplier tube and avalanched photodiode. Examples of multiple channel detectors include charged couple device. In one embodiment, the lateral flow device is as described above and is positioned within a Raman spectrometer capable of detecting Raman-active complexes in the detection zone. In another embodiment, the lateral flow device further includes a control zone and is positioned within a Raman spectrometer capable of detecting a Raman-active tag in the control zone.

The lateral flow device may be used to detect the presence of various target organisms or molecules, which may be dangerous or toxic, such as anthrax. Raman spectrometer detection system may generate information rich data. The vibrational data provides a spectral 'fingerprint'. Damage to sample is minimal or minimized. The samples can be analyzed relatively non-invasively, such as inside bottles and bags. Many samples can be analyzed 'as is' with minimal or no sample preparation. The analysis is relatively rapid; some samples may be analyzed in less than 60 seconds. Samples in differing forms can be analyzed, such as crystals, powders, and liquids with little or no reconfiguration of the detection system. Remote sensing is possible and is suited for fiber optic probes.

Figure 4:
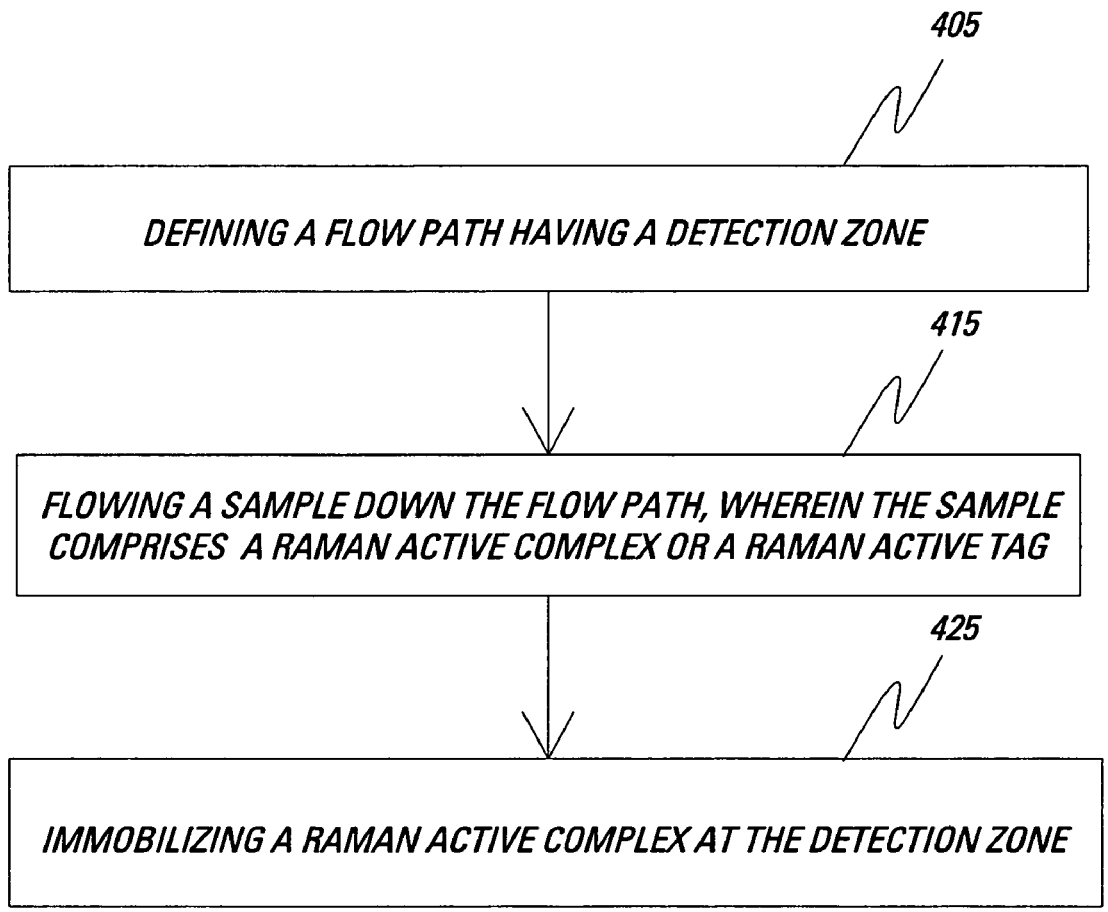
FIG. 4 is flow chart of a method of detecting the presence of a target in a sample in accordance with an embodiment of the invention.

With reference to FIG. 4, a method of conducting a lateral flow assay is described. Lateral flow assays and devices include, but are not limited to, immunochromatographic assays and strip-based immunoassays. The method, at Step 405, includes defining a flow path having a detection zone. In a particular embodiment, the flow path has a control zone down flow from the detection zone. Step 415 includes flowing a sample down the flow path. In one embodiment, the sample is deposited on the sample zone. The sample includes a Raman-active complex or a Raman-active tag. Step 425 includes immobilizing a Raman-active complex, if present, at the detection zone. In a particular embodiment, a Raman-active tag is also immobilized at the control zone.

The sample is placed in a sample zone and is drawn through a contact zone containing immuno-SERS particles against the target pathogen. Immobilized target-binding moieties (ie. immobilized pathogen-specific antibodies) in the detection zone bind the immuno-SERS-pathogen complexes. Immuno-SERS particles captured in a control zone are used as a positive control for reagent flow and SERS detection.

In one embodiment, the lateral flow assay further includes generating a Raman spectrum of the Raman-active complex from the detection zone. After a given time interval, the Raman spectrum may be taken. The method further includes correlating the Raman spectrum to the presence of a target attached to the Raman active complex. The method further includes correlating the Raman spectrum to the identification and or quantification of the target attached to the Raman active complex.

The sample may include a plurality of targets and the method of conducting the lateral flow assay includes being able to detect a plurality of targets, sequentially or simultaneously. Thus, in one embodiment, the sample includes a plurality of Raman-active complexes attached to a plurality of targets. The method further includes generating a plurality of Raman spectrums, wherein the plurality of Raman spectrums correlate to the presence or identification of targets that are different from each other. Detection, identification, and or quantification of the plurality of the targets is then based on correlating the plurality of Raman signals to the plurality of targets in the sample.

The method is not limited by how the Raman-active tag, target, or Raman-active complex are provided. In one embodiment, the Raman-active tags unattached to a target and Raman-active complex are simultaneously provided. In another embodiment, the Raman-active tags unattached to a target and Raman-active complex are sequentially provided. In one embodiment, the Raman-active complex is formed by providing a target and Raman-active tag, so that the Raman active complex is formed subsequently.

In one embodiment, immobilizing the Raman-active complex at the detection zone includes providing a detection zone having an immobilized target-binding moiety capable of attaching to the target of the Raman-active complex. Immobilizing the Raman-active tag at the control zone includes providing a control zone having an immobilized particle-binding moiety capable of attaching [t]one or more Raman-active tags. The method is not limited by how the Raman-active complex, Raman-active tags, and targets are immobilized at the detection and control zone. The method is also not limited by how the Raman-active complex, Raman-active tags, and targets attach. Examples of attaching include, but are not restricted to, electrostatically, chemically, and physically.

The following examples illustrate the features and advantages of the invention and is not intended to limit the invention thereto. Particularly, the examples demonstrate that it is possible to use immuno-functionalized Raman-active tags to detect the presence of a specific target organism in a lateral flow assay format. In these experiments, a Raman signal was only detected at the detection zone when the appropriate Raman-active complex attached to a target and a target-binding moiety immuno-functionalized for that specific target organism attached to the Raman-active complex were both present.

The detection of three varying targets with three differing Raman-active analytes are summarized in Table 1. The three differing targets are *Clostridium botulinum* toxoid, *Bacillus anthracis* (sterne), and *Francisella tularensis*. The three differing analytes are BPE, Quinoline thiol (QSH), and 4,4'-dipyridyl.

TABLE 1

SERS nanoparticle tags used to detect targets

| Example | SERS Tag | Target |
|---|---|---|
| 1 | Trans-bis(pyridyl)ethylene (BPE) | *Clostridium botulinum* toxoid |
| 2 | Trans-bis(pyridyl)ethylene (BPE) | *Bacillus anthracis* (sterne) |
| 3 | Quinoline thiol (QSH) | *Bacillus anthracis* (sterne) |
| 4 | 4,4'-dipyridyl | *Francisella tularensis* |

EXAMPLE 1

SERS-Based Detection of Botulinum Toxoid Using Lateral-Flow Test-Strips

Reagents

Reagents used were Botulinum toxoid solution and Raman-active tag. The Raman-active tags were SERS-active nanoparticles (Raman-active) directly attached to anti-botoxoid antibodies.

Method

The SERS-active anti botox particles were mixed with 50 ul of the toxoid solution to form a mixture. The mixture was incubated at room temperature for several minutes. A portion of the mixture was deposited onto the sample port of a lateral flow assay test for botulinum toxin and incubated at room temperature for 20 minutes. The lateral flow strip was analyzed for SERS signal and the signal intensity at test line was compared to the background intensity.

SERS spectra were obtained from the detection zone of lateral flow assays using anti botulinum toxin SERS particles (i.e. Raman active tag with anti botulinum toxin targeting moiety). The Raman-active analyte was bis(pyridyl)ethylene (BPE).

Figure 5:
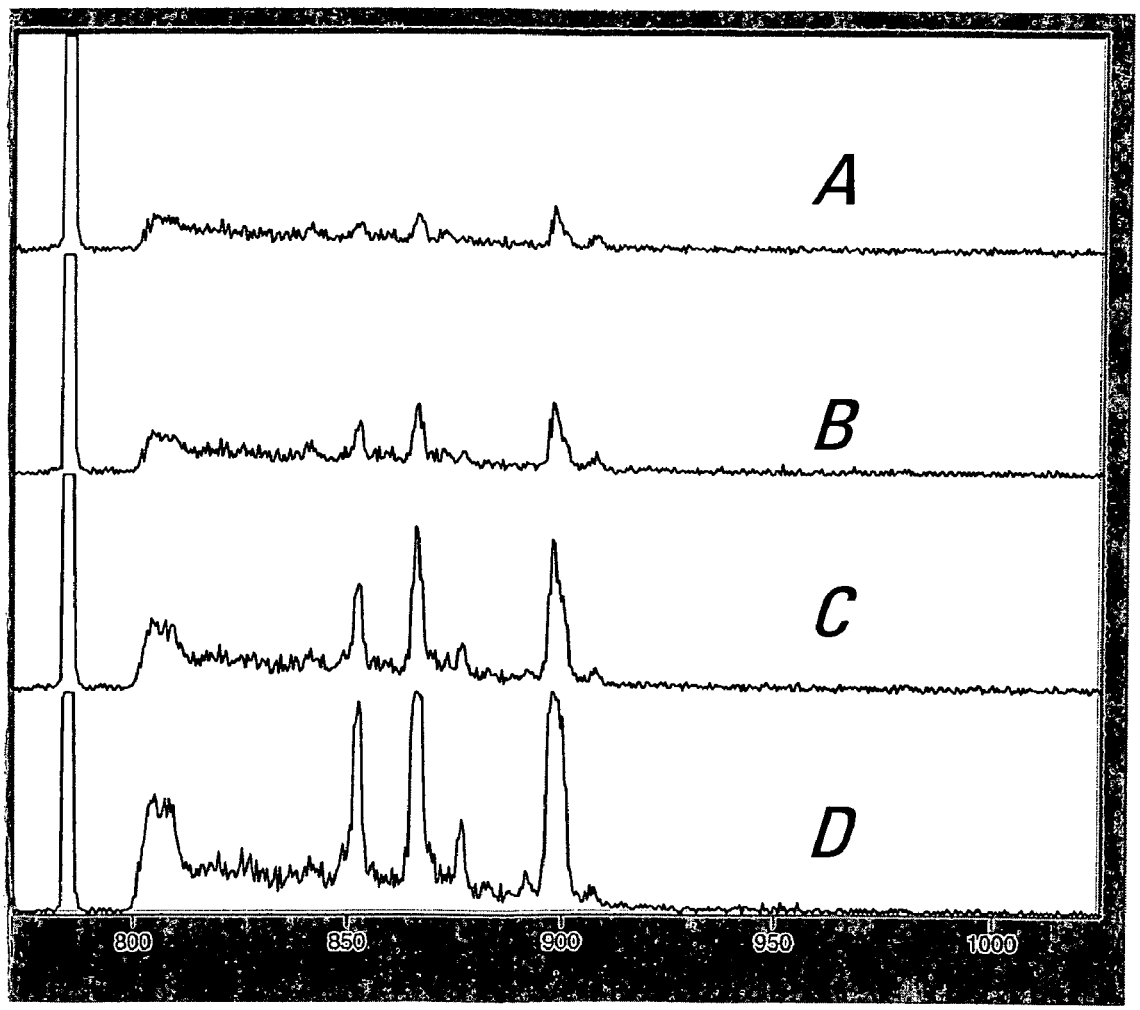
FIG. 5A is a background SERS (Surface Enhanced Raman Spectroscopy) spectrum obtained from a lateral flow assay other than the detection zone in accordance with an embodiment of the invention.
FIG. 5B is a SERS spectrum from a lateral flow assay detection zone in the presence of 1 ng of target molecule botulinum toxoid in accordance with an embodiment of the invention.
FIG. 5C is a SERS spectrum from a lateral flow assay detection zone in the presence of 10 ng of target molecule botulinum toxoid in accordance with an embodiment of the invention.
FIG. 5D is a SERS spectrum from a lateral flow assay detection zone in the presence of 100 ng of target molecule botulinum toxoid in accordance with an embodiment of the invention.

FIG. 5A is a background SERS spectrum obtained from a lateral flow assay other than from the detection zone. For FIG. 5A-5D, 6A-6C, 7A-7D, 8A-8B, and 9A-9B, the x-axis is wavelength in nm and the y-axis indicates the intensity of the SERS signal. There was a small amount of Raman signal due to non-specific binding of the Raman-active tag to the substrate.

FIG. 5B is a SERS spectrum obtained from a lateral flow assay detection zone in the presence of 1 ng of target molecule botulinum toxoid. The Raman-active tags immuno-functionalized with anti-botulinum toxin antibodies (target-binding moiety) attached to the target botulinum toxin and formed Raman-active complex. The detection zone had immobilized anti-botulinum toxin antibodies (immobilized target-binding moiety) which then retained the Raman-active complex at the detection zone. Consequently, there was a detectable Raman signal from the material collected from the detection zone which was significantly greater than the background.

FIG. 5C is a SERS spectrum obtained from a lateral flow assay detection zone in the presence of 10 ng of target molecule botulinum toxoid. Consequently, there was a detectable Raman signal from the material collected from the detection zone which was significantly greater than the background.

FIG. 5D is a SERS spectrum obtained from a lateral flow assay detection zone in the presence of 100 ng of target molecule botulinum toxoid. Consequently, there was a detectable Raman signal from the material collected from the detection zone which was significantly greater than the background.

Figure 6A:
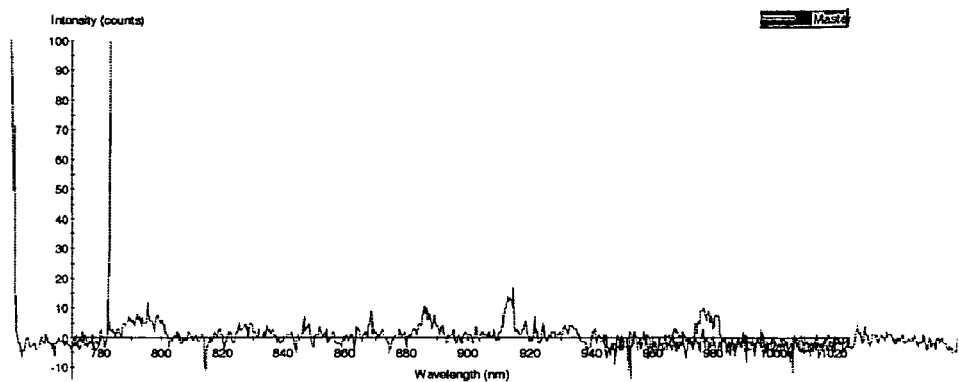
FIG. 6A is a background SERS spectrum obtained from a lateral flow assay other than the detection zone in accordance with an embodiment of the invention.
Figure 6B:
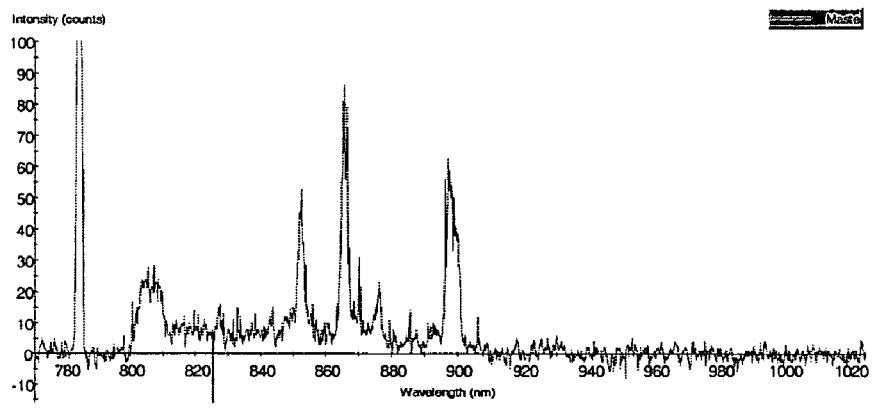
FIG. 6B is a SERS spectrum obtained from a lateral flow assay detection zone in the presence of target molecule botulinum toxoid in accordance with an embodiment of the invention.

Another trial with the target molecule botulinum toxoid and Raman active analyte BPE was also conducted to show repeatability and reproducibility. The data are as follows:

FIG. 6A is a background SERS spectrum obtained from a lateral flow assay other than from the detection zone. There was a small amount of Raman signal due to non-specific binding of the Raman-active tag to the substrate FIG. 6B is a SERS spectrum obtained from a lateral flow assay detection zone in the presence of target molecule botulinum toxoid. The Raman-active tags immuno-functionalized with anti-botulinum toxin antibodies (target-binding moiety) attached to the target botulinum toxin and formed Raman-active complex. The detection zone had immobilized anti-botulinum toxin antibodies (immobilized target-binding moiety) which then retained the Raman-active complex at the detection zone. Consequently, there was a detectable Raman signal from the material collected from the detection zone which was significantly greater than the background.

Figure 6C:
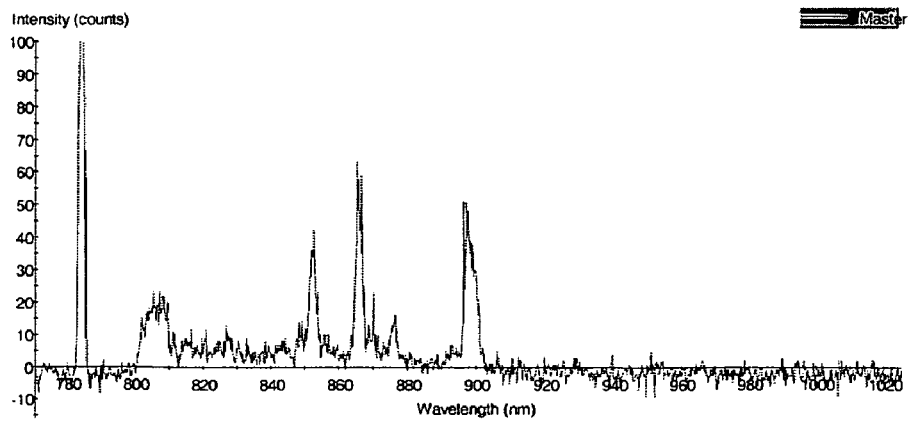
FIG. 6C is a SERS spectrum obtained from the lateral flow assay control zone in the presence of target molecule botulinum toxoid in accordance with an embodiment of the invention.

FIG. 6C is a SERS spectrum obtained from the control zone in the presence of target molecule. This is a positive control that shows the expected SERS spectrum of the Raman-active particle. The control zone had immobilized anti-Raman-active particle antibodies (immobilized target-binding moiety) which retained the Raman-active tag at the control zone. Consequently, there was a detectable Raman signal from the material collected from the control zone.

Thus, Example 1 demonstrates how it is possible to use immuno-functionalized Raman-active tags to detect the presence of a specific target organism 212. In these experiments, a significant Raman signal is only detected when the appropriate target organism 212 and Raman-active tags immuno-functionalized for that specific target organism to detect the presence of that specific target organism are both present.

EXAMPLE 2

SERS-Based Detection of Bacterial Spores Using Lateral-Flow Test-Strips

Reagents used were *Bacillus anthracis* vaccine strain spores and anti-anthrax-Raman-active tags. The Raman-active tags were SERS-active nanoparticles (Raman-active particle 110) directly attached to anti anthrax antibodies.

Approximately $1 \times 10^6$ spores (target molecule or organism) were mixed with the SERS-active anti anthrax tag to form a mixture. The mixture was incubated at room temp several minutes. A portion of the mixture was deposited onto the sample port of a lateral flow assay test for Anthrax spores and incubated at room temperature for 20 minutes. The lateral flow strip was analyzed for SERS signal and the signal intensity at the detection zone was compared to the background intensity. Visible lines at the detection zone and control zone were present due to accumulation of the SERS particles.

Figure 7:
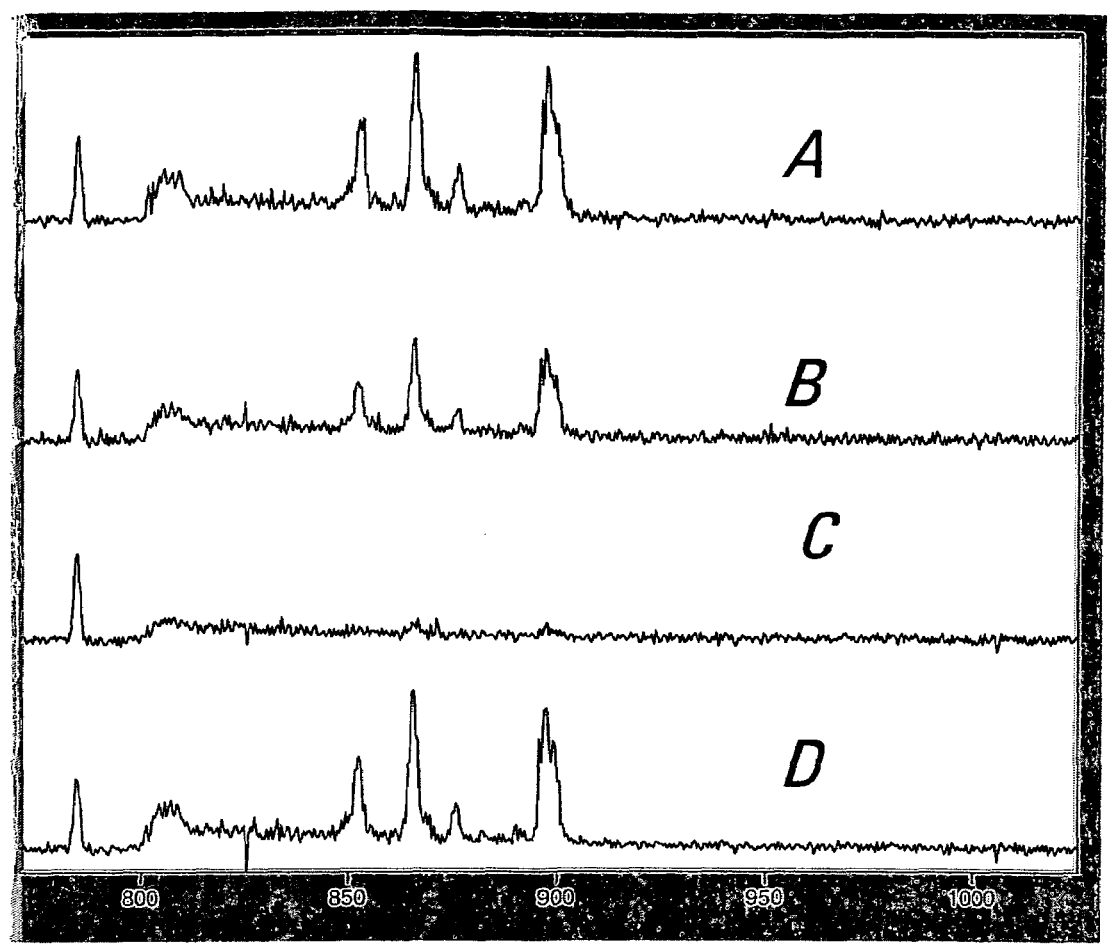
FIG. 7A is a SERS spectrum obtained from a lateral flow assay detection zone in the presence of bacterial spores using re-hydrated SERS tags to in accordance with an embodiment of the invention.
FIG. 7B is a SERS spectrum obtained from a lateral flow assay detection zone in the presence of bacterial spores using SERS tags lyophilized on a conjugate pad in accordance with an embodiment of the invention.
FIG. 7C is a background SERS spectrum obtained from a lateral flow assay other than the detection zone in accordance with an embodiment of the invention.
FIG. 7D is a SERS spectrum obtained from a lateral flow assay detection zone in the presence of bacterial spores using SERS tags in accordance with an embodiment of the invention.

FIG. 7A is a SERS spectrum obtained from a lateral flow assay detection zone in the presence of bacterial spores using re-hydrated SERS tags to detect bacterial spores. The Raman-active tags immuno-functionalized with anti-bacterial spores antibodies (target-binding moiety) attached to the target bacterial spores and formed Raman-active complexes. The detection zone contained immobilized antibodies against anthrax (immobilized target-binding moiety) which then retained the Raman-active complex at the detection zone. Consequently, there was a detectable Raman signal from the material collected from the detection zone which was significantly greater than a background signal in FIG. 7C.

FIG. 7B is a SERS spectrum obtained from a lateral flow assay detection zone in the presence of bacterial spores using SERS tags lyophilized on a conjugate pad to detect bacterial spores. Consequently, there was a detectable Raman signal from the material collected from the detection zone which was significantly greater than a background signal in FIG. 7C.

FIG. 7C is a background SERS spectrum obtained from a lateral flow assay other than from the detection zone. There was a small amount of Raman signal due to non-specific binding of the Raman-active tag to the substrate FIG. 7D is a SERS spectrum obtained from a lateral flow assay detection zone in the presence of bacterial spores using SERS tags to detect bacterial spores. Consequently, there was a detectable Raman signal from the material collected from the detection zone which was significantly greater than a background signal in FIG. 7C.

Thus, Example 2 demonstrates how it is possible to use immuno-functionalized Raman-active tags to detect the presence of another specific target organism, bacterial spores. In these experiments, a significant Raman signal was only detected when the bacterial spores and Raman-active tags immuno-functionalized for bacterial spores are both present.

EXAMPLE 3

Figure 8:
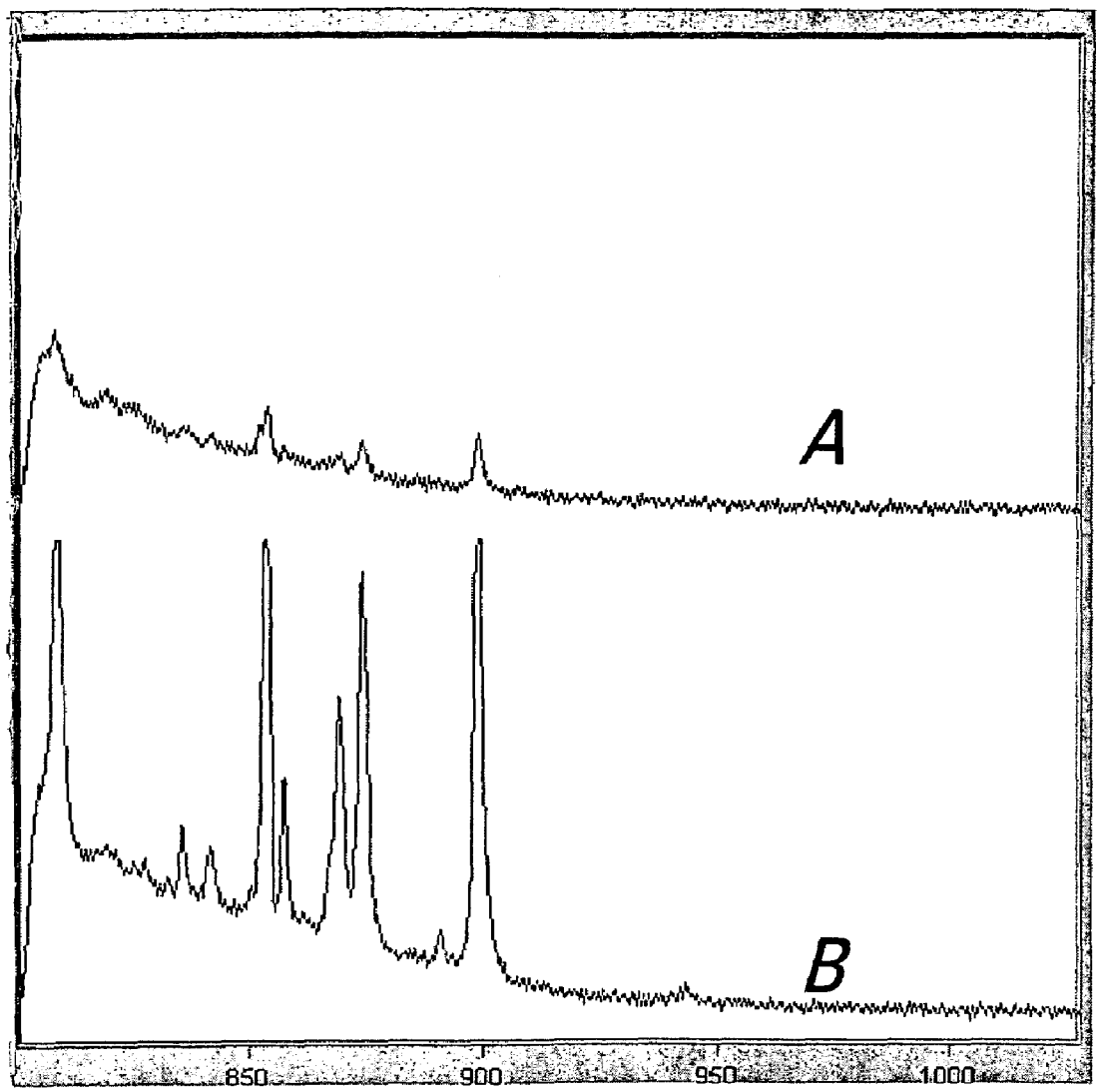
FIG. 8A is a background SERS spectrum obtained from a lateral flow assay other than the detection zone in accordance with an embodiment of the invention.
FIG. 8B is a SERS spectrum obtained from a lateral flow assay detection zone in the presence of target molecule bacterial spores in accordance with an embodiment of the invention.
Figure 9:
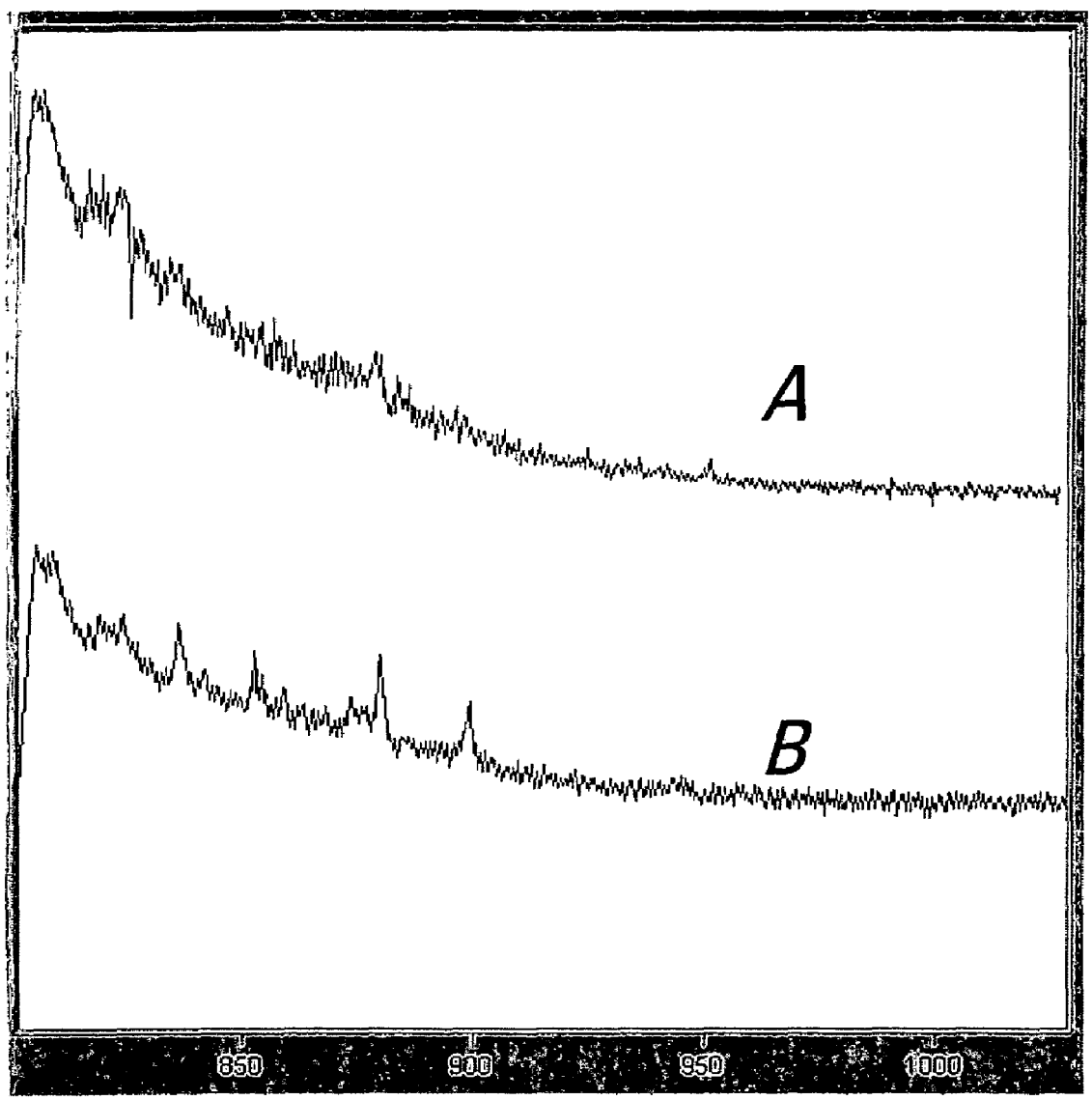
FIG. 9A is a background SERS spectrum obtained from a lateral flow assay area other than the detection zone in accordance with an embodiment of the invention.
FIG. 9B is a SERS spectrum obtained from a lateral flow assay detection zone in the presence of target molecule *F. tularensis* in accordance with an embodiment of the invention.

Example 3 demonstrates immuno-functionalized Raman-active tags can be used to detect the presence of a specific target organism with more than just one type of Raman active analyte, such as BPE. The presence of the specific target organism bacterial spores was detected with Raman-active tags that have a different Raman active analtye, DPY. In these experiments, a significant Raman signal was only detected when the bacterial spores and Raman-active tags immuno-functionalized for bacterial spores to detect the presence of bacterial spores are both present. FIG. 8A is a background SERS spectrum obtained from a lateral flow assay other than the detection zone. There was a small amount of Raman signal due to non-specific binding of the Raman-active tag to the substrate FIG. 8B is a SERS spectrum obtained from a lateral flow assay detection zone in the presence of target molecule bacterial spores. Consequently, there was a detectable Raman signal from the material collected from the detection zone which was significantly greater than a background signal in FIG. 8A.

EXAMPLE 4

Example 4 uses immuno-functionalized Raman-active tags to detect the presence of yet another specific target. The presence of the target organism *F. tularensis* was detected with Raman-active tags. In these experiments, a Raman signal was only detected when the *F. tularensis* and Raman-active tags immuno-functionalized for *F. tularensis* are both present.

FIG. 9A is a background SERS spectrum obtained from a lateral flow assay other than the detection zone. There was a small amount of Raman signal due to non-specific binding of the Raman-active tag to the substrate.

FIG. 9B is a SERS spectrum obtained from a lateral flow assay detection zone in the presence of target molecule *F. tularensis*. Consequently, there was a detectable Raman signal from the material collected from the detection zone which was significantly greater than a background signal in FIG. 9A.

While the invention has been described in detail in connection with only a limited number of aspects, it should be understood that the invention is not limited to such disclosed aspects. Rather, the invention can be modified to incorporate any number of variations, alterations, substitutions or equivalent arrangements not heretofore described, but which are commensurate with the scope of the claims. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A lateral flow device comprising:

a substrate having a flow path that utilizes capillary action to induce flow; and a non-metallic detection zone disposed along the flow path, wherein the detection zone comprises an immobilized target-binding moiety directed against a target of a Raman-active complex.

2. The lateral flow device of claim 1, wherein the target comprises at least one target selected from a group consisting of prokaryotic cells, eukaryotic cells, viruses, proteins, polypeptides, toxins, liposomes, nucleic acids, and beads.

3. The lateral flow device of claim 1, wherein the immobilized target-binding moiety comprises at least one moiety selected from a group consisting of antibodies, aptamers, nucleic acids, selective ligands, and polypeptides.

4. The lateral flow device of claim 1, wherein the detection zone comprises a plurality of immobilized target-binding moieties.

5. The lateral flow device of claim 4, wherein the plurality of immobilized target-binding moieties are directed against targets different from each other.

6. The lateral flow device of claim 1, wherein the detection zone comprises a plurality of detection zones.

7. The lateral flow device of claim 1, further comprising a control zone disposed along the flow path down flow from the detection zone, wherein the control zone comprises an immobilized particle-binding-moiety directed against a Raman-active tag.

8. The lateral flow device of claim 7, wherein the control zone comprises a plurality of immobilized particle-binding moieties.

9. The lateral flow device of claim 7, wherein the detection zone and control zone are at least partially spatially co-located.

10. The lateral flow device of claim 1, wherein the substrate comprises nitrocellulose membrane.

11. The lateral flow device of claim 1, wherein the target is attached to a plurality of Raman-active tags.

12. The lateral flow device of claim 1, wherein said Raman-active complex includes a tag that is SERS-active prior to becoming immobilized in the detection zone.

13. A detection system comprising:

a lateral flow device comprising:

a substrate having a flow path that utilizes capillary action to induce flow;

a detection zone disposed along the flow path, wherein the detection zone comprises an immobilized target-binding moiety directed against a target of a Raman-active complex, wherein said Raman-active complex includes a tag that is SERS-active prior to becoming immobilized in the detection zone; and a Raman spectrometer capable of detecting a Raman-active complex at the detection zone.

14. The detection system of claim 13, wherein the lateral flow device further comprises a control zone disposed along the flow path down flow from the detection zone, wherein the control zone comprises an immobilized particle-binding-moiety directed against a Raman-active tag.

15. The detection system of claim 13, wherein the detection zone comprises a plurality of immobilized target-binding moieties directed against targets different from each other.

16. The detection system of claim 13, wherein the detection zone is non-metallic.

17. A method of conducting a lateral flow assay comprising:

i) defining a flow path having a non-metallic detection zone;

ii) flowing a sample down the flow path via the use of capillary action, wherein the sample comprises a Raman-active complex or a Raman-active tag;

iii) immobilizing a Raman-active complex, if present, at the detection zone; and iv) outputting a signal indicative of the Raman-active complex immobilized at the detection zone, said signal being capable of being detected at the detection zone.

18. The method of claim 17, further comprising generating a Raman spectrum of the Raman-active complex from the detection zone.

19. The method of claim 18, further comprising correlating the Raman spectrum to a presence of a target.

20. The method of claim 19,further comprising correlating the Raman spectrum to an identification of the target.

21. The method of claim 19, further comprising correlating the Raman spectrum to a quantity of the target.

22. The method of claim 17, wherein the sample comprises a plurality of Raman-active complexes attached to a plurality of targets.

23. The method of claim 22, further comprising generating a plurality of Raman spectrums, wherein the plurality of Raman spectrums correlate to the presence of a plurality of targets different from each other.

24. The method of claim 23, further comprising correlating the plurality of Raman spectrums to an identification of the plurality of targets different from each other.

25. The method of claim 23, further comprising correlating the plurality of Raman spectrums to a quantification of the plurality of targets different from each other.

26. The method of claim 15, wherein flowing the sample comprising providing the Raman-active tags unattached to a target and Raman-active complex simultaneously.

27. The method of claim 17, wherein flowing the sample comprising providing the Raman-active tags unattached to a target and Raman-active complex sequentially.

28. The method of claim 17, wherein the Raman-active complex is provided by a target and Raman-active particle.

29. The method of claim 17, wherein immobilizing the Raman-active complex at the detection zone comprises providing a detection zone having an immobilized target-binding moiety capable of attaching to the target of the Raman-active complex.

30. The method of claim 17, further comprising a control zone down flow from the detection zone and immobilizing a Raman-active tag at the control zone, said signal being capable of attaching to the Raman-active tag.

31. The method of claim 30, wherein immobilizing the Raman-active tag at the control zone comprises providing a control zone having an immobilized particle-binding moiety capable of attaching to the Raman-active tag.

32. The method of claim 17, wherein the target-binding moiety comprises at least one moiety selected from a group consisting of antibodies, aptamers, nucleic acids, selective ligands, and polypeptides.

33. The method of claim 17, wherein the Raman-active tag comprises a tag that is SERS-active prior to becoming immobilized in the detection zone.

34. A method of detecting the presence of a target, comprising:
i) conducting a lateral flow assay having a flow path, wherein the flow path has a plurality of detection zones;
ii) flowing a sample down the flow path via the use of capillary action, wherein the sample comprises a Raman-active complex including a tag that is SERS-active prior to reaching the plurality of detection zones; and wherein the sample is suspected of having a plurality of targets; and
iii) outputting a signal indicative of the Raman-active complex at the plurality of detection zones, said signal being capable of being detected at the plurality of detection zones.

35. The method of claim 34, further comprising immobilizing a Raman-active complex, if present, at the detection zone.

36. The method of claim 34, wherein the plurality of detection zones are non-metallic.

* * * * *

UNITED STATES PATENT AND TRADEMARK OFFICE
CERTIFICATE OF CORRECTION

PATENT NO. : 7,518,721 B2
APPLICATION NO. : 11/223353
DATED : April 14, 2009
INVENTOR(S) : Burrell et al.

It is certified that error appears in the above-identified patent and that said Letters Patent is hereby corrected as shown below:

In Column 5, Line 32, after "100 nm" insert -- . --.

In Column 12, Line 13, delete "[t]one" and insert -- one --, therefor.

In Column 14, Line 66, delete "analtye," and insert -- analyte, --, therefor.

In Column 17, Line 11, in Claim 26, delete "15," and insert -- 17, --, therefor.

Signed and Sealed this

Thirtieth Day of June, 2009

JOHN DOLL
*Acting Director of the United States Patent and Trademark Office*